United States Patent [19]
Guay et al.

[11] Patent Number: 5,226,185
[45] Date of Patent: Jul. 13, 1993

[54] THERAPEUTIC HOUSEHOLD BED MATTRESS

[76] Inventors: Yvan R. Guay, 1231, Ste-Catherine West, Suite 2000, Montreal, Quebec, Canada, H3G 1P5; Gilles M. Lévesque, 1618, Captentier, Boisbriand, Quebec, Canada, J7G 2Y7

[21] Appl. No.: 918,756

[22] Filed: Jul. 27, 1992

[51] Int. Cl.⁵ .................. A61N 1/00; A47C 27/00
[52] U.S. Cl. ............................ 5/448; 5/471; 5/906; 600/15
[58] Field of Search ............ 5/448, 462, 471, 906, 5/500, 502; 600/9, 15; 252/62.54

[56] References Cited

U.S. PATENT DOCUMENTS

| | | | |
|---|---|---|---|
| 4,042,986 | 8/1977 | Goodman et al. | 5/500 |
| 4,143,435 | 3/1979 | Masuda | 600/9 X |
| 4,317,244 | 3/1982 | Balfour-Richie | 5/500 X |
| 4,330,892 | 5/1982 | Fukushima | 5/906 X |
| 4,489,711 | 12/1984 | Latzke | 600/15 |
| 4,509,219 | 4/1985 | Yagi | 5/906 X |
| 4,549,532 | 10/1985 | Baermann | 600/15 |
| 4,782,540 | 11/1988 | Parker | 5/471 X |
| 4,924,542 | 5/1990 | Yamaguchi | 5/906 X |
| 5,035,017 | 7/1991 | Komuro | 5/448 X |
| 5,105,490 | 4/1992 | Shek | 5/448 |

FOREIGN PATENT DOCUMENTS 3522667  1/1987  Fed. Rep. of Germany ........ 600/15

OTHER PUBLICATIONS

Translation of German patent #3522667 to Horst Baermann published Jan. 8, 1987.

*Primary Examiner*—Michael F. Trettel
*Attorney, Agent, or Firm*—Roland L. Morneau

[57] ABSTRACT

A covering for bed mattress comprising a plastic foam layer and a quilted layer superposed on the foam layer and a plurality of flat permanent magnetic bans adheringly mounted under the foam layer. The magnetic bands are located at predetermined distances from each other and are made of permanent fine magnetic particles embedded in a rubber-like flexible thermoplastic binder. The layers have a total thickness of about 2 to 5 inches and the magnets have an induction of about 1250 to 3850 gauss. The magnetic bands are disposed along a plurality of parallel rows and the magnetic bands of each row are disposed in staggered relationship with the magnetic bands of adjacent rows. The magnetic bands are preferably rectangular with a width of about 2 to 3 inches and a length of about 5 to 8 inches. The distance between each band and between each adjacent row is about 10 to 15 inches. The covering provides therapeutic benefits to the human body.

13 Claims, 3 Drawing Sheets

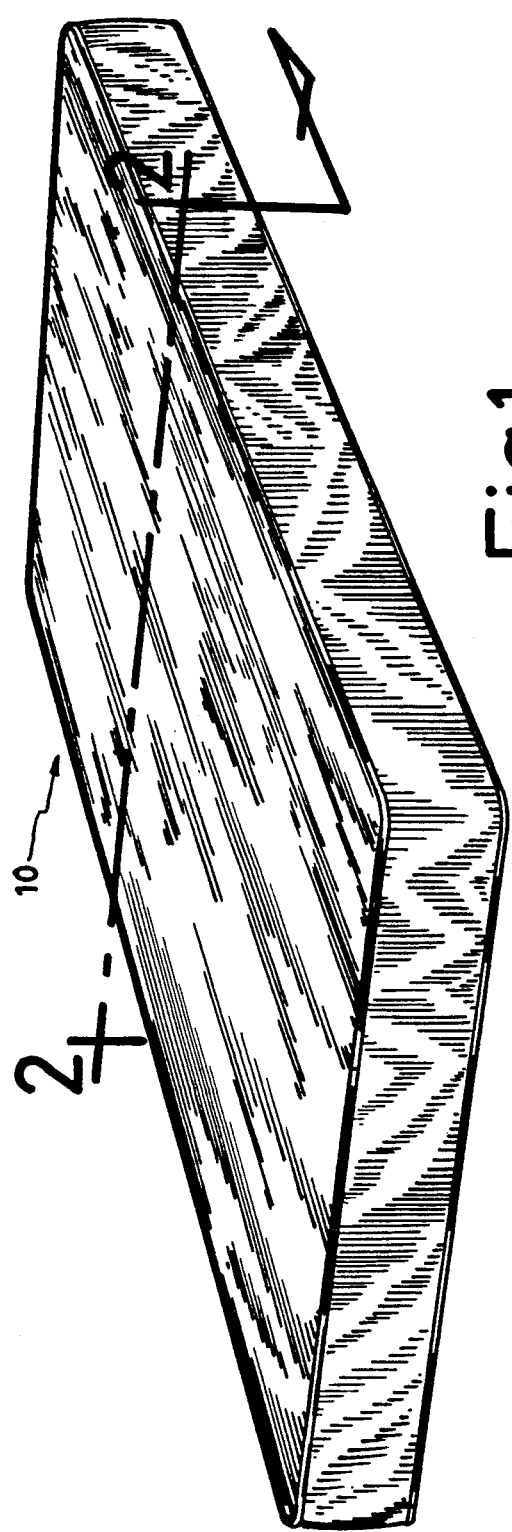
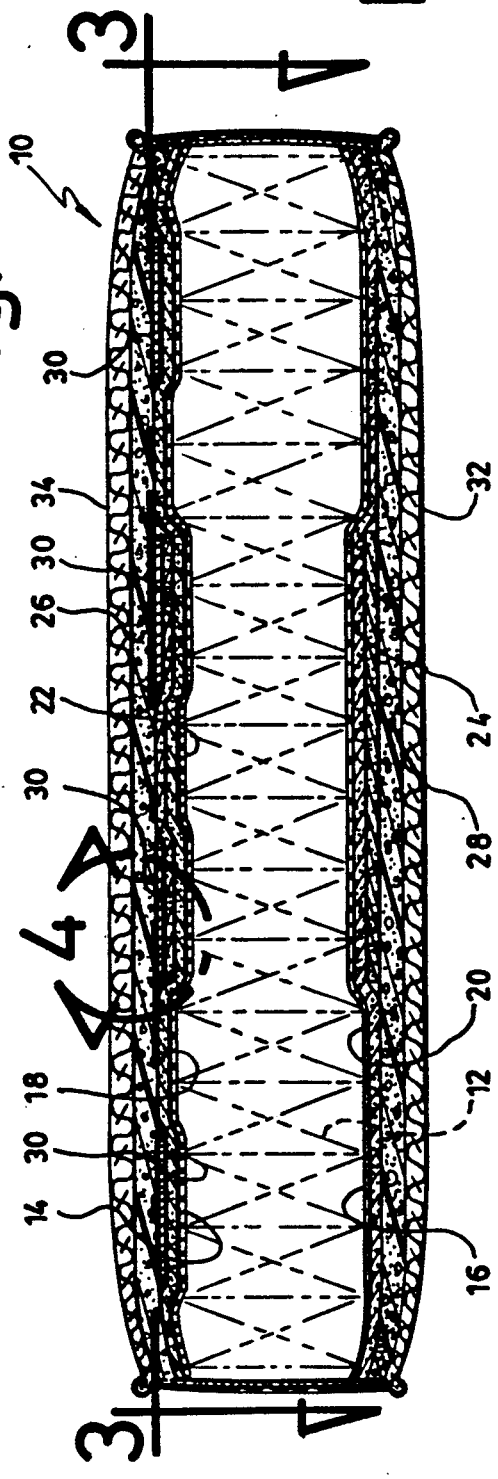

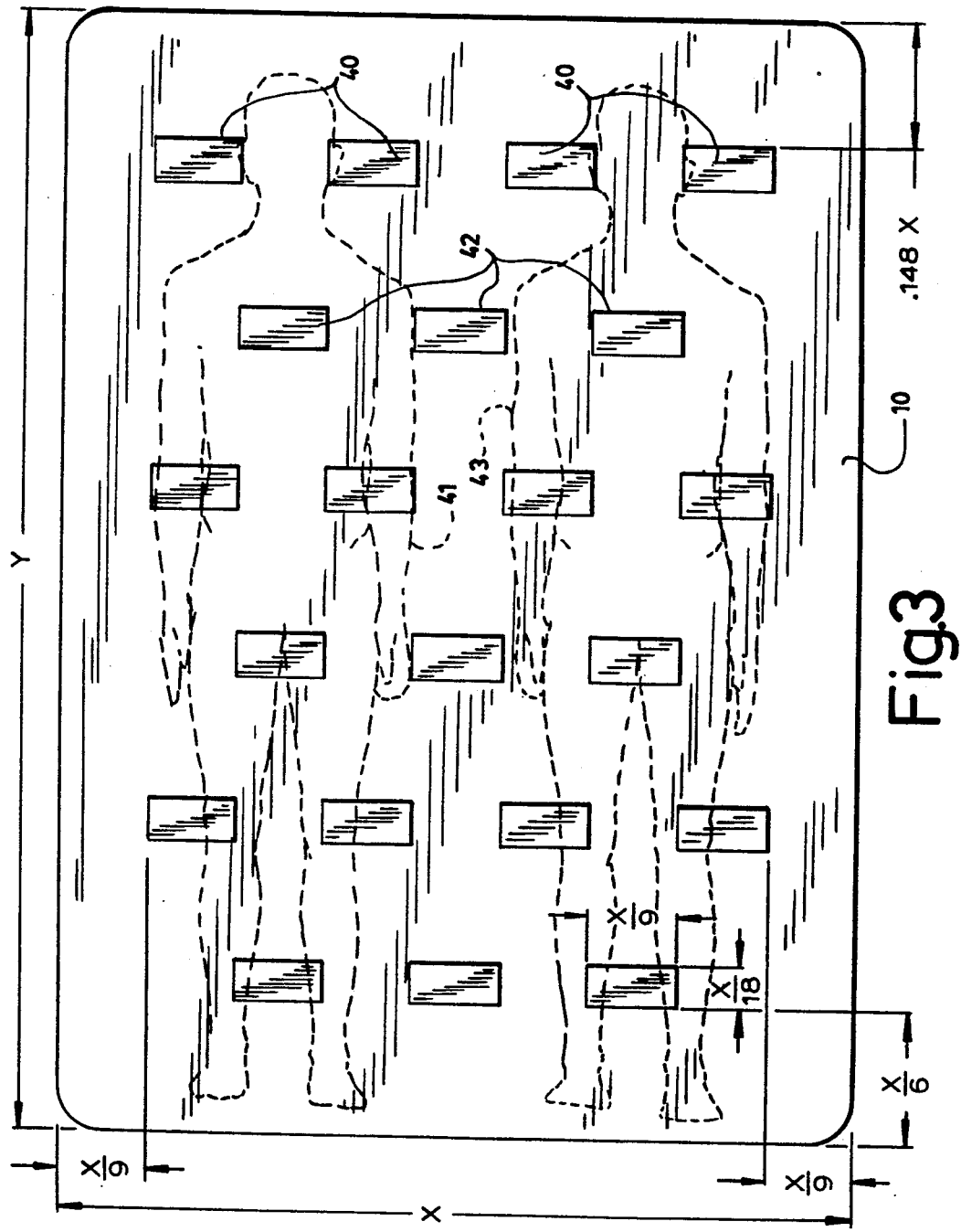

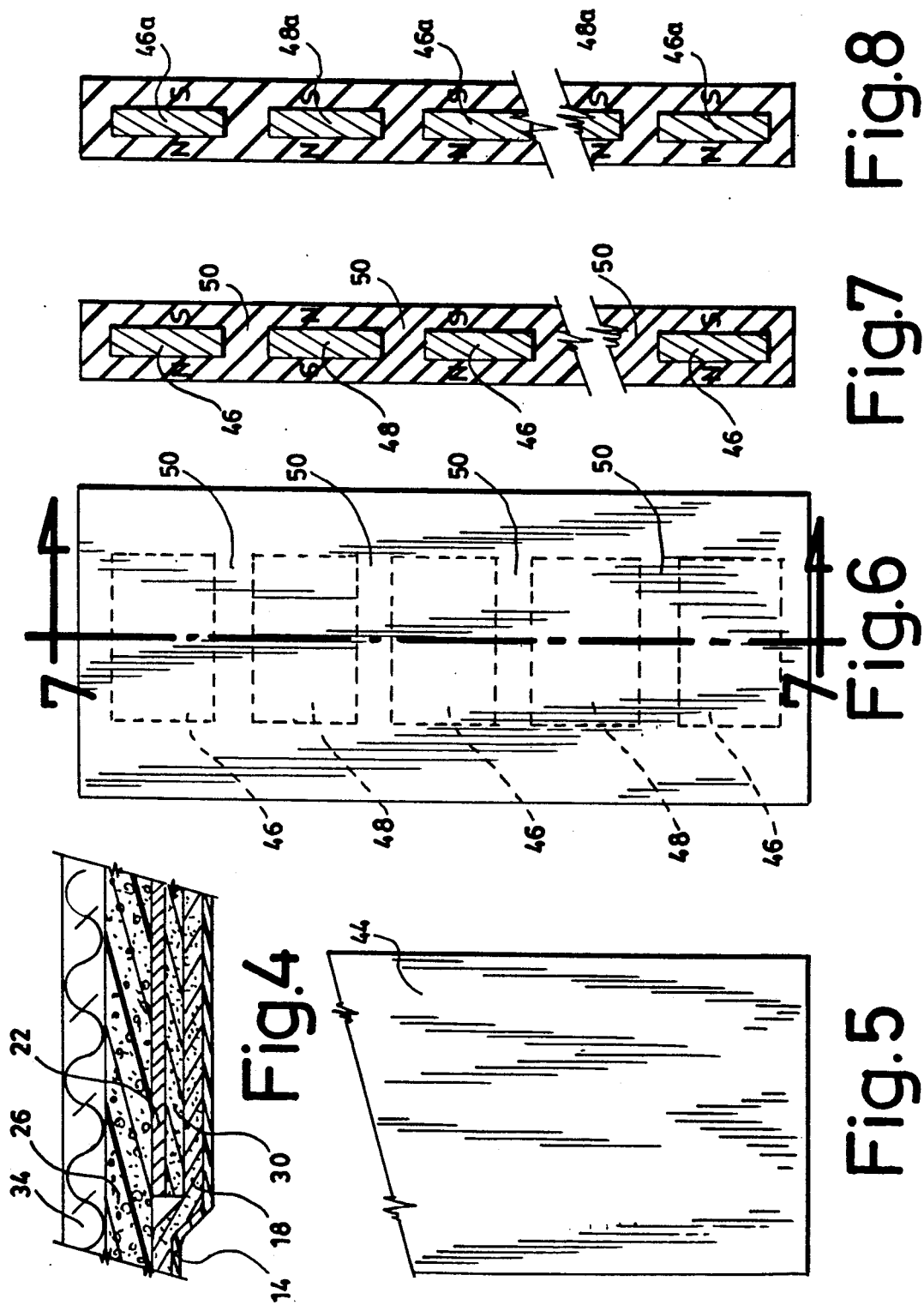

THERAPEUTIC HOUSEHOLD BED MATTRESS

BACKGROUND OF THE INVENTION

1. Field of the invention

The present invention is directed to a bed mattress provided with a plurality of magnetic bands distantly fixed below the upper layers of the mattress. The magnetic bands are of a type to generate micro-pulsions of a predetermined range of inductions and are disposed away from a human body lying on a bed to allow him to receive therapeutic benefits during extensive periods of time without counterindications to most people.

The type of magnetic bands contemplated do not hinder the comfort of a person who can spend a full night sleep without presenting any risk of durable or recurrent side affects on the human body.

The present mattress provided with magnets having a residual magnetic induction within prescribed ranges and distances are safe and can afford a high rate of improvement in case of biological rates troubles and bad sleeping.

It has also been found that the micro-pulsions generated can accelerate the rate of healing of bone fractures particularly in the case of recalcitrant fractures.

It is accordingly an object of the present invention to combine such magnets with a natural human environment which is a household bed and which consists in allowing a person to benefit from such micro-pulsions during his sleep without having to wear usually heavy auxilliary therapeutic clothing during relatively short periods of time. While lying in bed, the body is in a state of rest which allows him to benefit more extensively from the therapeutic advantages of the magnetic induction.

Considering that the therapeutic benefits include the relief of chronic tiredness, a specific combination of magnetic bands with a household bed mattress within a specific arrangement provides a synergetic effect to the curing of such illness.

2. Prior art

U.S. Pat. No. 5,017,185 to Baermann discloses flexible magnetic strips which are specifically directed to be used in tubular shape wrapped around body sections for providing magnetic field lines adapted to pass through the body sections enclosed therein. Baermann specifies in this patent the range of density of the magnetic field as being 130 Gauss with foils having a thickness of 3 mm. Such a range of density and thickness differs drastically from the ones of the present application. The range of periods of wearing time, although not specified, may not need to be specified because of the extremely low magnetic induction.

Published Canadian application No. 2,006,319 entitled "Magnetic Massage Therapeutic Device" by Susie Dragan is directed to a device including an arrangement of permanent magnets and flexible coils for generating a low-frequency field from a pulse generator of predetermined frequency and amplitude for activating the magnets. The magnets are used in apron-like covers and oral inserts which are in close proximity with the human body and for short periods of time. Even when Susie Dragan foresees the use of magnets, in combination of a bed, the latter is surrounded by a generator, Such complex combination implies that it is used for relatively short treatment periods of time and certainly not for a daily household bed use for a complete night sleep.

SUMMARY OF THE INVENTION

The invention is directed to a bed mattress comprising a plastic foam layer and a quilted layer superposed on the foam layer and a plurality of flat perminent magnetic bands adheringly mounted under the foam layer. The magnetic bands are located at predetermined distances from each other and are made of permanent fine magnetic particles embedded in a rubber-like flexible thermoplastic binder. The layers have a total thickness of about 2 to 5 inches and the magnets have an induction of about 1250 to 3850 gauss.

The magnetic bands are disposed along a plurality of parallel rows and the magnetic bands of each row are disposed in staggered relationship with the magnetic bands of adjacent rows. The magnetic bands are preferably rectangular with a width of about 2 to 3 inches and a length of about 5 to 8 inches. The distance between each band and between each adjacent row is about 10 to 15 inches.

BRIEF DESCRIPTION OF THE DRAWINGS

FIG. 1 is a perspective view of a bed mattress according to the invention,

FIG. 2 is a vertical cross-sectional view taken through line 2—2 of the bed mattress shown in FIG. 1, FIG. 3 is a cross-sectional view along line 3—3 of FIG. 3, FIG. 4 is an enlarged view of encircled portion 4 of FIG. 2, FIG. 5 is a portion of an enlarged view of one embodiment of a magnetic band, FIG. 6 is an enlarged view of a second embodiment of a magnetic band, and, FIGS. 7 and 8 are two cross-sectional views along line 7—7 of two different embodiments of the magnetic band shown in FIG. 6.

DETAILED DESCRIPTION OF THE INVENTION

FIG. 1 is a perspective view of a mattress 10 according to the invention which displays essentially a similar outer appearance as a conventional mattress.

As illustrated schematically in FIG. 2, the core 12 of the mattress may be made of a plurality of coil springs, a foam rubber, a water or an air bag.

When the core 12 is made of coil springs, an upper and a lower netting 14 and 16 completely cover the springs 12. The nettings 14 and 16 have a flat plastic latticed structure displaying apertures of less than one inch square. The object of the nettings 14 and 16 is to protect the superposed layers from wearing out due to the sharpness of the springs.

An upper and a lower felt fabric 18 and 20 extends over the surface of the nettings 14 and 16 which completely closes the apertures in the latticed structure. A second felt fabric 22 and 24 may also be added to cover the central portion of the mattress so as to further rigidify the most flexible portion of the coil springs 12.

An upper and lower foam layer 26 and 28 is disposed to cover the felt fabrics 18 and 20 over the whole surface of the bed 10 under which a plurality of magnetic bands 30 have been adheringly mounted. The foam layers 26 and 28 are generally made of polyurethane having a high density of about 2.25 to 2.5 pounds per square foot to maintain a substantial thickness when a person lies on the mattress. The foam layers 26 and 28 are preferably made of an eggshell design to increase the thickness of each layer 26 and 28.

The uppermost and lowermost layers of the mattress 10 consisting of a quilt 32 and 34 extends over the whole surface of the upper foam layer 28. The quilts 32 and 34 which include a soft spongy substance stitched between two layers of textile fabric is generally covered with a ticking for wrapping all the superposed layers including the lateral, perimetric stitched sides of the mattress 10.

The felt fabrics 18, 20, 22 and 24 are essentially contemplated for protecting the magnetic bands 30 from the wear caused by the sharpness of the endmost spirals of the coil springs 12. The foam layer 26 and the quilt 34 are contemplated to provide a thick padded surface over the magnetic bands 30 so as to exceed a minimum spacing between the magnetic bands 30 and the human body which is expected to lie over the surface of the mattress 10. In order to provide substantially the minimum thickness of the layers 26 and 34, the quilted layer 34 is defined as having a minimum thickness of about ½ of an inch while the foam cover 26 has a minimum thickness of about 1½ to 2 inch.

The thickness of the padded surface comprising the quilt 34 and the foam layer 26 is determined relative to the intensity of the magnetic bands 30. For a total thickness of the layers 26 and 34 varying between 2 and 13 inches, the induction of the magnetic bands is contemplated to proportionately vary between 1250 to 3850 gauss. Such proportion allows a person to spend extensive periods of time lying on the bed mattress 10 according to the invention without any counterindication as stated above.

The magnetic bands 40 as illustrated in FIG. 3 are disposed along rows parallel to adjacent rows of bands 42 and are located in a staggered position relative to each other. The number of magnetic bands are sufficient to essentially cover the whole surface of the bed mattress 10 while being spaced from each other depending on their size and their induction intensity. As an example, magnetic bands having a rectangular shape with dimensions of 2 to 3 inches in width and 4 to 8 inches in length, may be distanced by about 12 inches within the same row of bands 40 and by about 11 inches with an adjacent row of bands 42. For magnetic bands having about 1850 gauss and each measuring 3 by 6 inches disposed under a pair of layers 26 and 34 having a thickness of not less than about 4.5 inches provides therapeutic benefits while a person lies on the mattress 10 for extensive periods of time such as a full night sleep. This allows the person to fall asleep and be in a state of rest while the magnetic micro-pulsions provide the therapeutic benefits desired.

The sleep is not hindered by the thickness of the bands 40 and 42 which is usually about 1 to 2 mm. They are generally glued on the foam layer 26.

FIG. 3 illustrates a specific embodiment for a double bed having a width of 54 inches and a length of 75 inches. For such a size bed, the bands are dimensioned at about a width of x/18 and a length of x/9, x representing the width of the mattress.

For a single bed having a mattress of about 39 inches in width, the dimensions of the bands are about x/6 by x/13.

For both of these embodiments the margins around the mattress which is free of magnetic bands vary from about x/4 to x/6 along the length and from about x/8 to x/9 along the width.

Considering that the bed mattress usually have standard sizes, these proportions may be represented by dimensions within substantially specific ranges.

Two human bodies 41 and 43 are schematically illustrated in FIG. 3 relative to the disposition of the magnetic bands.

The magnetic bands 40 are disposed in rows alternating with adjacent rows of magnetic bands 42 and the magnetic bands of one row are staggered relative to the magnetic bands of the adjacent row. The distance between two bands of the same row substantially corresponds to the length of the bands. The distance between two adjacent rows from center to center, substantially corresponds to the distance, center to center, of two adjacent bands of the same row. For bands of 3×6 inches, the bands of the same row are distant by about 12 inches and the bands of adjacent rows are distant by about 11 inches.

Such configuration provides a suitable repartition of the desired magnetic effect on the human body.

The embodiment of the magnetic band 44 shown in FIG. 5 is made of randomly dispersed magnetic particles in a rubber base. The particles are polarized perpendicularly across the band 44 i.e. one face corresponding to the north pole and the other face corresoponding to the south pole.

As shown in FIG. 6, the magnetic bands are made of a plurality of adjacently and transversely positioned, ribbon-like magnets similarly or alternately polarized with the adjacent ones. Each ribbon-like magnet is made of permenant fine magnetic particles embedded in a rubber-like flexible thermoplastic carrier. Each adjacent ribbon-like magnet 46 and 48 are flexibily connected to each other by a rubber-like material or a flexible textile material 50 allowing each magnet and interconnection to flex along its length and between each other so as to be freely flexible along the full length and width of the magnetic bands 30. The flexibility of the embedding material is important considering that the bands must be bendingly responsive to the coil springs 12 and to the shape of the human bodies 40 and 43 lying over them.

The strips 46a and 48a are disposed in an alternately polarized configuration as shown in FIGS. 8 which provides a continuous interaction between adjacent strips 46a and 48a and creating micro-pulsions within their environment.

Although the present mattress has been illustrated and described with a core made of coil springs 18, the same novel covering is equally suitable for mattress having a core made of plastic foam or for water bed mattresses. In fact, the novel covering described provides the desired results if laid on any substantially flat surface without a specific combination with a core.

For all the types of cares, when rectangular magnetic bands are used, the longest axis of the bands is preferably disposed across the width of the mattress. Such a disposition allows a more suitable flexibility of the bands when one or two persons rest on the mattress.

We claim:

1. A covering for bed mattress comprising a plastic foam layer and a quilted layer superposed on said foam layer and a plurality of flat permanent magnetic bands adheringly mounted under said foam layer, said magnetic bands being located at predetermined distances relative to each other, said magnetic bands being made of permanent fine magnetic particles embedded in a rubber-like flexible thermoplastic binder and an induction of about 1250 to 3850 gauss, both of said layers having a total combined thickness of about 2 to 13 cm.

2. A covering for bed mattress as recited in claim 1, wherein said magnetic bands have a rectangular shape axially disposed along a plurality of parallel rows, the magnetic bands of each row being disposed in staggered relationship with the magnetic bands of adjacent rows.

3. A covering for bed mattress as recited in claim 2, wherein said magnetic bands have a width of about 2 to 3 inches and a length of about 4 to 8 inches and the distance between each other and each adjacent row is about 10 to 15 inches.

4. A covering for bed mattress as recited in claim 3, wherein the magnetic bands have a dimension of about 3×6 inches, are distant from each other by about 12 inches within the same row and are distant by about 11 inches from one row to an adjacent row, said rows of magnets adapted to extend substantially over the full upper surface of the mattress.

5. A covering for bed mattress as recited in claim 4, wherein each magnetic band has an induction of about 1850 gauss.

6. A covering for bed mattress as recited in claim 2, wherein said quilted layer includes a sheet of foam rubber, said magnetic bands being adheringly mounted on said sheet.

7. A covering for bed mattress as recited in claim 2, wherein the southpoles of the magnetic bands are all directed in the same direction.

8. A bed mattress as recited in claim 3, wherein the length of the bands extend across the width of the mattress.

9. A bed mattress having a plastic foam layer, a quilted layer superposed on said foam layer and a plurality of flat, permanent magnetic rectangular bands adheringly mounted under said foam layer, the combined thickness of said layers being about 5 to 13 cm, said magnetic bands disposed in quincunx along a plurality of spaced linear columns and rows, said columns and rows being displayed over the full surface of the foam layer, each magnetic band having dimensions of about 3×6 inches and being laterally spaced from each other, center to center, by about 12 inches, each row being spaced from each other, center to center, by a distance of about 11 inches, the columns of each alternate row being disposed substantially midway between the column of the adjacent rows, each of said bands being made of a plurality of closely spaced, juxtaposed, flexible, ribbon-like, alternately polarized magnets, each ribbon-like magnet of the same band being flexibly connected together to follow the shape of the layers when a person lies over said mattress, said bands having an induction of about 1250 to 3850 gauss.

10. A bed mattress as recited in claim 9, wherein said ribbon-like magnets are made of permanent fine magnetic particles embedded in a rubber-like flexible thermoplastic material.

11. A bed mattress as recited in claim 10, wherein said ribbon-like magnets of each band are joined together by a rubberized textile material.

12. A bed mattress as recited in claim 9, wherein said bands have an induction of about 1850 to 2000 gauss.

13. A bed mattress as recited in claim 9, wherein the lateral sides of the bands of one row are substantially aligned with the lateral sides of the bands of the adjacent rows.

* * * * *